United States Patent [19]

LaMattina et al.

[11] 4,302,464
[45] Nov. 24, 1981

[54] IMIDAZOLYLPYRIDINE THERAPEUTIC AGENTS

[75] Inventors: John L. LaMattina, Ledyard; Christopher A. Lipinski, Waterford, both of Conn.

[73] Assignee: Pfizer Inc., New York, N.Y.

[21] Appl. No.: 197,388

[22] Filed: Oct. 16, 1980

[51] Int. Cl.$^3$ .................. A61K 31/44; C07D 401/04
[52] U.S. Cl. .................................... 424/263; 546/278
[58] Field of Search .................. 546/278; 424/263

[56] References Cited
PUBLICATIONS

Gilman, Organic Chemistry, vol. IV, John Wiley, p. 729.

Patterson, J. Am. Chem. Soc. (1925), vol. 47, pp. 543–546.

Schunack, Arch. Pharmaz., vol. 306, pp. 934–942, (1973).

Yamada et al., Yakugaku Zasshi, vol. 95 (No. 5), 1975, pp. 487–492.

Primary Examiner—Henry R. Jiles
Assistant Examiner—Bernard Dentz
Attorney, Agent, or Firm—Charles J. Knuth; Peter C. Richardson; James M. McManus

[57] ABSTRACT

A series of 2-substituted-4-(4-imidazolyl)pyridines and the pharmaceutically acceptable acid addition salts thereof as histamine $H_2$-receptor inhibitors for controlling gastric acidity.

14 Claims, No Drawings

IMIDAZOLYLPYRIDINE THERAPEUTIC AGENTS

BACKGROUND OF THE INVENTION

1. Field of the Invention

This invention relates to novel medicinal agents and their use in a pharmaceutical composition. In particular, the invention concerns 2-substituted-4-(4-imidazolyl)-pyridines and a pharmaceutical composition for their use as anti-ulcer agents.

2. Description of the Art

In the past, various attempts have been made by investigators in the field of organic medicinal chemistry to obtain new and better anti-ulcer agents. For the most part, these efforts have involved the synthesis and testing of various heretofore new and unavailable organic compounds, particularly in the area of organic heterocyclic bases, in an endeavor to determine their ability to inhibit the secretion of gastric acid in the stomach without causing any substantial anticholinergic side effects to occur that might possibly be considered undesirable from a pharmacological point of view. However, in the search for newer and still better or more improved anti-ulcer agents, far less is known about the effect (particularly on peptic ulcers) of other organic compounds in this area which could proceed in the body via a non-anticholinergic mechanism and yet still possess gastric acid antisecretory properties. Nevertheless, G. J. Durant et al., in U.S. Pat. Nos. 4,022,797, 4,024,271 and 4,027,026 do disclose that certain histamine $H_2$-receptor inhibitors in the thioalkyl-, aminoalkyl- and oxyalkylguanidine series and in the pyridyl-substituted thioalkyl- and oxyalkylthiourea series, respectively, are useful for these purposes even though these particular compounds are not known to be anticholinergic per se. These particular histamine $H_2$-receptor inhibitors all function by antagonizing those responses to histamine, such as the stimulation of the secretion of gastric acid in the stomach, which cannot be blocked by the action of a histamine $H_1$-receptor antagonist like mepyramine, for example. As a result, these compounds are definitely of value as histamine $H_2$-receptor inhibitors for controlling gastric acidity and are therefore useful in the treatment of peptic ulcers and other like conditions of the body, etc.

Yamada, et al., Yakugaku Zasshi, 95 (5), 487 (1975) (C.A. 83, 113633r) has reported the preparation of 4-(4-pyridyl)imidazole as a by-product in the reaction of 4-pyridylcarbinol and formaldehyde, while Schunack, Arch. Pharmaz. 306, 934 (1973) has reported the same compound as an intermediate in the synthesis of compounds having "histamine-like" activity.

SUMMARY OF THE INVENTION

It has now been discovered that certain 2-substituted-4-(4-imidazolyl)pyridines and their pharmaceutically acceptable acid addition salts are useful as anti-ulcer agents by virtue of their controlling gastric acidity. These compounds are of the formulae:

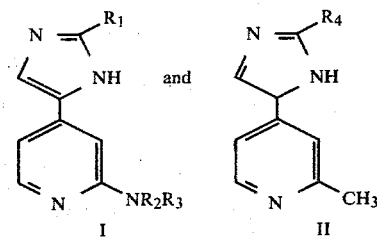

and the pharmaceutically acceptable acid addition salts thereof, where $R_1$ is hydrogen, alkyl of one to three carbon atoms or amino; $R_2$ and $R_3$ are each hydrogen, alkyl of one to three carbon atoms or phenylalkyl where said alkyl contains one to three carbon atoms; and $R_4$ is methyl or amino.

A preferred group are those compounds of formula I where $R_2$ is hydrogen and $R_3$ is said alkyl. Especially preferred within this group are 2-ethylamino-4-(2-amino-4-imidazolyl)pyridine, 2-ethylamino-4-(4-imidazolyl)pyridine, 2-ethylamino-4-(2-methyl-4-imidazolyl)pyridine and 2-ethylamino-4-(2-ethyl-4-imidazolyl)pyridine.

A second preferred group of compounds of formula I are those wherein $R_2$ and $R_3$ are each said alkyl. Especially preferred within this group are 2-dimethylamino-4-(4-imidazolyl)pyridine and 2-dimethylamino-4-(2-amino-4-imidazolyl)pyridine.

A third group of preferred compounds of formula I are those wherein $R_2$ and $R_3$ are each hydrogen. Especially preferred is 2-amino-4-(4-imidazolyl)pyridine.

Preferred compounds of formula II are 2-methyl-4-(2-methyl-4-imidazolyl)pyridine and 2-methyl-4-(2-amino-4-imidazolyl)pyridine.

Also within the scope of the present invention is a pharmaceutical composition suitable for oral administration which is comprised of a pharmaceutically acceptable carrier and a therapeutic amount of an anti-ulcer agent selected from those of formulae I and II.

DETAILED DESCRIPTION OF THE INVENTION

In accordance with the processes employed in the synthesis of the 2-substituted-4-(4-imidazolyl)pyridines of the present invention, compounds of formula I wherein $R_1$ is hydrogen are prepared by the following scheme:

In practice, the 2-amino-4-(2-mercapto-4-imidazolyl)-pyridine in a reaction-inert solvent, is contacted with Raney nickel. The weight ratio of mercaptan to Raney nickel is about 1:4, respectively.

The reaction-inert solvent utilized in this process should be one which solubilizes to some extent the reactants and does not react to any appreciable extent with either the reactants or the products formed. Such solvents or mixtures thereof which meet this criteria are N,N-dialkyl amides of alkanoic acids, such as dimethylformamide, dimethylacetamide and N-methyl-2-pyrrolidone and also hexamethylphosphoramide. In general it is preferred that highly polar, aprotic solvents be employed.

The reaction time is not critical and is dependent on reaction temperature and inherent reactivity of the starting reagents. At temperatures of 100°–150° C., the reaction is essentially complete in three to six hours.

The product can be isolated by filtration of the nickel and concentration of the filtrate to dryness. Further purification of the product is effected by recrystallization from a solvent or solvents or by chromatographing on florisil.

The requisite 2-amino-4-(2-mercapto-4-imidazolyl)-pyridines employed as the reactants leading to the products of the present invention are prepared by conventional reactions as hereinafter described.

Compounds of formula I wherein $R_1$ is amino and of formula II wherein $R_4$ is amino are prepared by the following scheme:

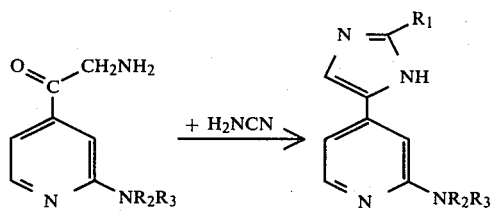

I ($R_1$ = $NH_2$)

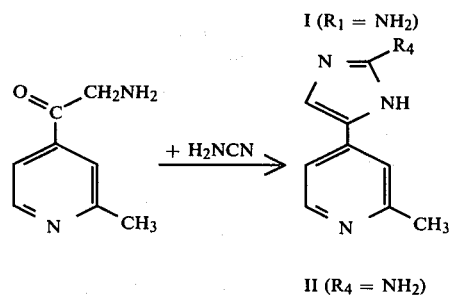

II ($R_4$ = $NH_2$)

In practice, the requisite 2-substituted 4-aminoacetylpyridine as an acid addition salt is contacted with cyanamide at a pH of about 4.5 in a reaction-inert solvent.

The molar ratio of reactants should be at least equivalent, but it is preferred that an excess of cyanamide be employed. Accordingly, a 100% excess of said reactant hastens the completion of the reaction without having any deleterious effect on the quality of the product.

It is preferred that the reaction be heated so that the time necessary to complete the reaction will not be unduly long. For convenience, steam bath temperatures have been used with a corresponding reaction time of about one hour.

The preferred solvent for the reaction is water, since said solvent solubilizes the reactants and does not react under the reaction conditions to any appreciable extent with either the reactants or the product.

It is preferred that the reaction be carried out at a pH of from about 4.0 to about 5.0 with a preferred pH of 4.5. This preferred pH can be achieved either by adding an inorganic base to an aqueous solution of the 4-aminoacetylpyridine di-acid addition salt, or by treating a suspension of the requisite aminoketone with an inorganic acid. The former method is preferred since such bifunctional compounds as aminoketones are known to polymerize as free bases.

Following the completion of the reaction, the medium is made basic by the addition of concentrated ammonium hydroxide and the mixture concentrated to dryness. The product is isolated from any inorganic salts by extraction with i-propanol. Removal of the alcohol provides the desired product, which may be further purified by conventional recrystallization.

The appropriate 2-substituted-4-aminoacetylpyridine reactants leading to compounds of the present invention are synthesized by conventional reactions known to those skilled in the art and are hereinafter described.

Compounds of formula I wherein $R_1$ is said alkyl and of formula II wherein $R_4$ is methyl are prepared by the following scheme:

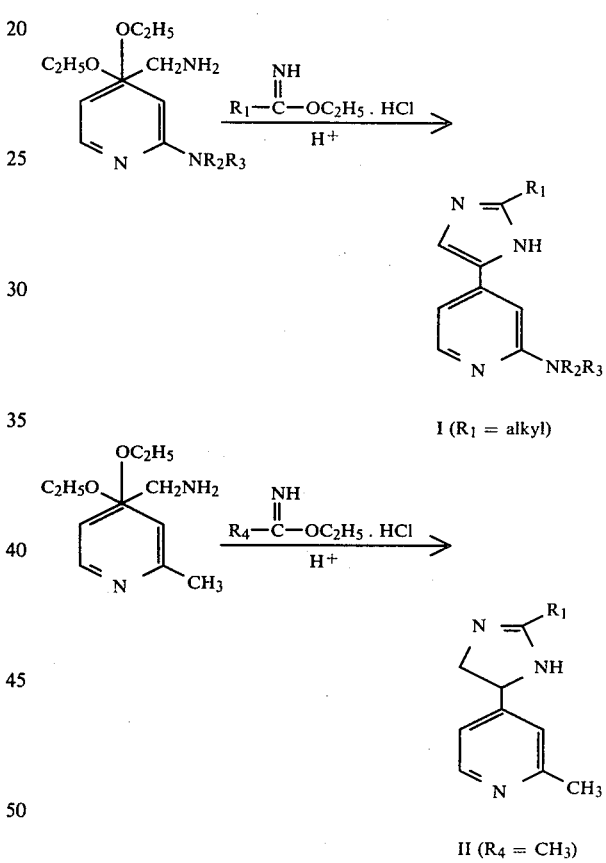

I ($R_1$ = alkyl)

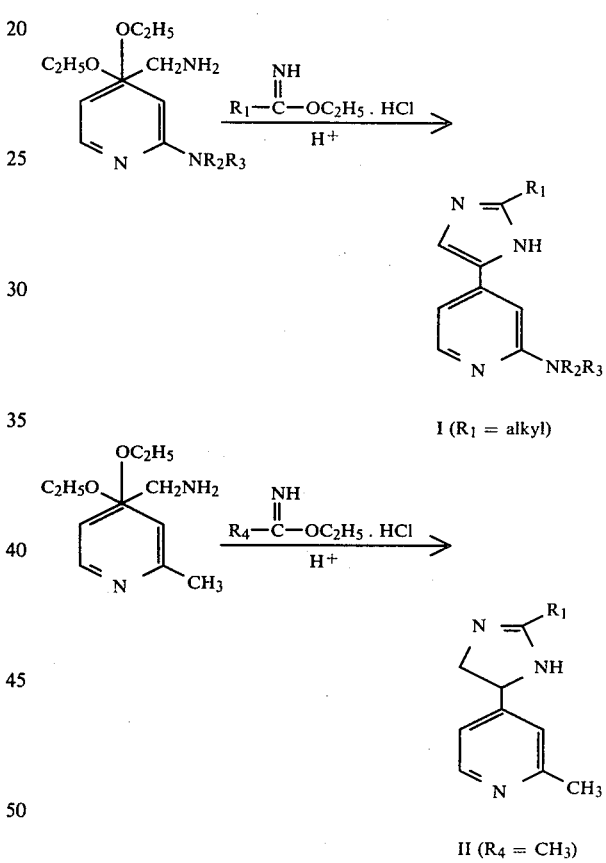

II ($R_4$ = $CH_3$)

The process comprises the reaction of a 2-(2-substituted-4-pyridyl)-2,2-diethoxyethylamine with an imidate hydrochloride in a reaction-inert solvent. Approximately equimolar amounts of the reactants are employed in this reaction, with as much as a 10% excess of the imidate ester.

The preferred solvents for the reaction are alkanols, especially methanol or ethanol. Other solvents can be employed provided they solubilize the reactants to an appreciable extent and do not undergo any reactions with the reactants or products under the conditions of the reaction.

The initial phase of the reaction is carried out at a temperature of about 50°–120° C. with a reaction time of about 1 to 6 hours.

Following the initial phase of the reaction, the solvent is removed and the intermediate is taken up in concentrated hydrochloric acid and heated for about one hour at steam bath temperatures. On completion of the reaction the acid is neutralized, usually with a solid inorganic base, and the product extracted into a water immiscible solvent, such as methylene chloride or chloroform.

The product, remaining after the solvent is removed, is purified by recrystallization or chromatographing on silica gel.

The ethylamine reactant is readily prepared by known reaction methods as hereinafter described, and the imidates are prepared by known procedures, such as those reported by Wagner and Zook, "Synthetic Organic Chemistry", John Wiley & Sons, Inc., New York, N.Y. 1953, Chapt. 21, p. 634.

The pharmaceutically acceptable acid addition salts of the 2-substituted-4-(4-imidazolyl)pyridine base compounds of this invention are prepared by simply treating the aforementioned organic bases with various mineral and organic acids which form nontoxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt-formation step may be carried out by simply using the proper molar amount of the appropriate acid in an aqueous solvent medium or in a suitable organic solvent such as methanol or ethanol. Upon careful evaporation of the solvent, the solid salt is readily obtained.

As previously indicated, the 2-substituted-4-(4-imidazolyl)pyridine compounds of this invention are all readily adapted to therapeutic use as histamine $H_2$-receptor inhibitors for the control of peptic ulcers, especially in view of their ability to inhibit the secretion of gastric acid in the body to a statistically significant degree. The compounds of the present invention have been found to consistently inhibit the pentagastrin-induced secretion of gastric acid from stomachs of Heidenhain pouch dogs to a significantly high degree when given by the intravenous route of administration at dose levels ranging from 1.0 mg./kg. to 10 mg./kg., respectively, without showing any substantial signs of toxic side effects. Furthermore, all the herein described compounds of this invention can be administered orally, for the present purposes at hand, without causing any significant untoward pharmacological side reactions to occur in the subject to whom they are so administered. In general, these compounds are ordinarily administered at dosage levels ranging from about 0.5 mg. to about 50 mg. per kg. of body weight per day, although variations will necessarily occur depending upon the condition and individual response of the subject being treated and the particular type of pharmaceutical formulation chosen.

In connection with the use of the 2-substituted-4-(4-imidazolyl)pyridine compounds of this invention for the treatment of subjects afflicted with peptic ulcers, it is to be noted that they may be administered either alone or in combination with pharmaceutically acceptable carriers and that such administration can be carried out in both single and multiple dosages. More particularly, the novel compounds of this invention can be administered in a wide variety of different dosage forms, i.e., they may be combined with various pharmaceutically acceptable inert carriers in the form of tablets, capsules, lozenges, troches, hard candies, powders, aqueous suspensions, elixirs, syrups and the like. Such carriers include solid diluents or fillers, sterile aqueous media and various non-toxic organic solvents, etc. Moreover, such standard pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

For purposes of parenteral administration, solutions or suspensions of the instant compounds in sesame or peanut oil or in aqueous propylene glycol solutions can be employed, as well as sterile aqueous solutions. These particular solutions are especially suited for intramuscular and subcutaneous injection purposes. The aqueous solutions dissolved in pure distilled water are also useful for intravenous injection purposes provided that their pH is properly adjusted beforehand. Such isolations should also be suitably buffered, if necessary, and the liquid diluent first rendered isotonic with sufficient saline.

The activity of the compounds of the present invention, as anti-ulcer agents, is determined by their ability to pass at least one of the following two standard biological and/or pharmacological tests, viz., (1) measuring their ability to antagonize those particular actions of histamine which are not blocked by an antihistamine such as mepyramine, i.e., a measure of their ability to block certain histamine $H_2$-receptor sites, and (2) measuring their ability to inhibit gastric acid secretion in the stomachs of Heidenhain pouch dogs that had previously been treated with pentagastrin in order to stimulate the secretion of said acid (in their stomachs) for these particular purposes.

The following examples are provided solely for the purpose of further illustration. Nuclear magnetic resonance spectra (NMR) were measured at 60 MHz for solutions in deuterochloroform ($CDCl_3$), perdeutero dimethyl sulfoxide (DMSO-$d_6$) or deuterium oxide ($D_2O$) or are noted otherwise, and peak positions are expressed in parts per million (ppm) downfield from tetramethylsilane or sodium 2,2-dimethyl-2-silapentane- 5-sulfonate. The following abbreviations for peak shapes are used: s, singlet; d, doublet; t, triplet; q, quartet; m, multiplet.

EXAMPLE I

2-Amino-4-(4-imidazolyl)pyridine

A. 1-(2-chloro-4-pyridyl)ethanone

To a stirred solution of 34.6 g. (0.25 mole) of 2-chloroisonicotinonitrile in 500 ml. of dry ether under a nitrogen atmosphere was added dropwise over 15 minutes 166 ml. of 3.0 M (0.5 mole) solution of methyl magnesium bromide. After stirring at room temperature for 24 hours the precipitate was filtered and added immediately to a mixture of 600 g. of ice and 300 ml. of water to which had been added 150 ml. of 6 N hydrochloric acid. The aqueous phase was extracted ($4 \times 100$ ml.) with ether and the combined ether extracts dried and concentrated to an oil. The residual oil was extracted with warm petroleum ether ($4 \times 50$ ml.) and the extracts combined and cooled in a dry ice/acetone bath. The resulting precipitate was filtered and dried to give 21.3 g. (55%) of the desired intermediate, m.p. 36°–38° C.

B. 1-(2-chloro-4-pyridyl)-1-ethylenedioxyethane

A mixture of 21.3 g. (0.137 mole) of 1-(2-chloro-4-pyridyl)ethanone and 0.5 g. of p-toluenesulfonic acid in 40 ml. of ethylene glycol and 300 ml. of toluene was placed in a flask fitted with a Dean-Stark trap and condenser, and was heated at reflux temperature for 16 hours. The mixture was cooled and concentrated in vacuo to give an oil which was purified by distillation under reduced pressure, 23.6 g. (86%), b.p. 65° C. (0.05 torr).

Anal. Calc'd. for $C_9H_{10}ClNO_2$: C, 54.2; H, 5.1; N, 7.0. Found: C, 54.1; H, 5.0; N, 7.2.

C. 1-(2-hydrazino-4-pyridyl)-1-ethylenedioxyethane

A mixture of 11.4 g. (57 mmoles) of 1-(2-chloro-4-pyridyl)-1-ethylenedioxyethane in 50 ml. of 98% hydrazine hydrate was heated to reflux for 15 hours. The mixture was cooled at 0° C. for 2 hours and the resulting precipitate was filtered and dried to give 10.3 g. (92%) of the desired compound. The analytical sample was recrystallized from toluene-cyclohexane.

Anal. Calc'd. for $C_9H_{13}N_3O_2$: C, 55.4; H, 6.7; N, 21.5. Found: C, 55.1; H, 6.6; N, 21.0.

D. 1-(2-amino-4-pyridyl)-1-ethanone

A mixture of 9.56 g. (49 mmoles) of 1-(2-hydrazino-4-pyridyl)-1-ethylenedioxyethane and 35 g. of Raney nickel in 150 ml. of absolute ethanol was shaken in a hydrogen atmosphere at an initial pressure of 3 atms. at room temperature for 4 hours. The catalyst was filtered and the filtrate concentrated to give 1-(2-amino-4-pyridyl)-1-ethylenedioxyethane as a white solid, m.p. 123°–126° C. The residual material was dissolved in 60 ml. of 2 N hydrochloric acid and heated at 75° C. for 3 hours. The mixture was cooled, neutralized with sodium bicarbonate and extracted with chloroform (30 ml. $\times$ 6). The combined extracts were dried and concentrated to give a pale yellow solid, which on recrystallization from toluene gave 5.0 g. (75%) of 1-(2-amino-4-pyridyl)-1-ethanone, m.p. 133°–133.5° C.

Anal. Calc'd. for $C_7H_8N_2O$: C, 61.8; H, 5.9; N, 20.6. Found: C, 61.9; H, 6.0; N, 20.6.

E. 1-(2-amino-4-pyridyl)-1-ethanone oxime

To a solution of 3.1 g. (45 mmoles) of hydroxylamine hydrochloride in 10 ml. of water was added 22.5 ml. of 2 N sodium hyroxide solution. To this solution was added 3.6 g. (26 mmoles) of 1-(2-amino-4-pyridyl)-1-ethanone and the mixture heated to the boiling point for 5 minutes. Methanol was added slowly until the mixture became homogeneous. Heating was continued until a precipitate began to form. The mixture was cooled to 0° C., and the resulting precipitate was filtered, washed with water and dried in vacuo. Recrystallization from ethyl acetate afforded 3.6 g. (92%) of the desired oxime, m.p. 215°–217° C.

Anal. Calc'd. for $C_7H_9N_3O$: C, 55.6; H, 6.0; N, 27.8. Found: C, 55.6; H, 6.1; N, 27.6.

F. 4-(2-amino-4-pyridyl)imidazole-2-thiol

To 720 mg. (31 mmoles) of sodium dissolved in 60 ml. of absolute ethanol at room temperature was added 4.59 g. (30.4 mmoles) of 1-(2-amino-4-pyridyl)-1-ethanone oxime, and the resulting mixture allowed to stir for about 5 minutes. To the resulting solution was added 6.10 g. (32 mmoles) of p-toluenesulfonyl chloride and the reaction mixture allowed to stir for 1 hour under a nitrogen atmosphere. The mixture was then added directly to a solution of potassium ethoxide (prepared by dissolving 1.41 g. of potassium in 30 ml. of ethanol) in ethanol and the reaction mixture allowed to stir under a nitrogen atmosphere at room temperature for 0.5 hour. The resulting gelatinous suspension was diluted with 800 ml. of diethyl ether, stirred at room temperature for 0.5 hour and filtered through celite. The filtrate was concentrated, and the residue taken up in 100 ml. of ether which was then extracted with 2 N hydrochloric acid ($4 \times 25$ ml.). The combined acid extracts were concentrated to a yellow solid, which was dissolved in 60 ml. of water containing 5.83 g. (60 mmoles) of potassium thiocyanate. The resulting solution was heated on steam bath temperatures for 2 hours. On cooling a solid precipitated which was filtered and stirred in 40 ml. of a saturated sodium bicarbonate solution for 0.5 hour. The solids were filtered, washed with water and dried in vacuo to give 3.21 g. (55%) of the product as a yellow solid, m.p. 262°–264° C. The analytical sample was recrystallized from water.

Anal. Calc'd. for $C_8H_8N_4S \cdot H_2O$: C, 45.7; H, 4.8; N, 26.6. Found: C, 45.5; H, 4.9; N, 26.2.

G. 2-amino-4-(4-imidazolyl)pyridine

To a solution of 2.3 g. (12 mmoles) of 4-(2-amino-4-pyridyl)imidazole-2-thiol in 60 ml. of dimethylformamide was added 8 g. of Raney nickel and the mixture heated at 115° C. for 3 hours. The mixture was filtered and the filtrate concentrated to a brown solid. After trituration with boiling chloroform, the solid was taken up in 50 ml. of absolute ethanol, treated with charcoal and the filtered solution concentrated to a small volume. The precipitate was filtered and dried, 1.12 g. (60%), m.p. 193°–196° C. The analytical sample was prepared by chromatographing on Florisil TM using chloroform-methanol (9:1, v:v) as the eluent, m.p. 196°–198° C.

Anal. Calc'd. for $C_8H_8N_4 \cdot \frac{1}{4}H_2O$: C, 58.3; H, 5.2; N, 34.0. Found: C, 58.5; H, 5.0; N, 34.0.

EXAMPLE II

2-Ethylamino-4-(4-imidazolyl)pyridine

A. 1-(2-ethylamino-4-pyridyl)-1-ethanone

A mixture of 18.8 g. (94 mmoles) of 1-(2-chloro-4-pyridyl)-1-ethylenedioxyethane and 50 ml. of ethylamine in 80 ml. of N-methyl-2-pyrrolidinone was sealed in a steel bomb and heated at 165° C. for 15 hours. The bomb was cooled and the contents distilled under reduced pressure to remove excess solvent. The residue in 100 ml. of methylene chloride was extracted with 2 N hydrochloric acid (3×25 ml.). The combined acid extracts were heated at 80° C. for 3 hours and were then cooled and made basic with sodium carbonate. The basified mixture was extracted with methylene chloride (4×25 ml.), and the combined organic extracts dried over sodium sulfate and evaporated to an oil which solidified, 11.5 g. (75%), m.p. 55°–57° C. The analytical sample was recrystallized from cyclohexane, m.p. 62°–63° C.

Anal. Calc'd. for $C_9H_{12}N_2O$: C, 65.8; H, 7.4; N, 17.1. Found: C, 65.5; H, 7.3; N, 17.1.

B. 1-(2-ethylamino-4-pyridyl)-1-ethanone oxime

To a mixture of 7 g. (0.1 mole) of hydroxylamine hydrochloride in 40 ml. of water and 50 ml. of 2 N sodium hydroxide was added 11.5 g. (70 mmoles) of 1-(2-ethylamino-4-pyridyl)-1-ethanone, and the resulting mixture heated to boiling. Methanol was carefully added until the mixture became homogeneous. Heating was continued until the mixture became cloudy. The mixture was cooled and the resulting precipitate filtered, washed with water and dried. Recrystallization from toluene gave 10.9 g. (87%) of the desired product, m.p. 155°–156° C.

Anal. Cald'd. for $C_9H_{13}N_3O$: C, 60.3; H, 7.3; N, 23.5. Found: C, 59.9; H, 7.3; N, 23.6.

C. 4-(2-ethylamino-4-pyridyl)imidazole-2-thiol

To 20 ml. of absolute ethanol containing 240 mg. of dissolved sodium was added 1.79 g. (10 mmoles) of 1-(2-ethylamino-4-pyridyl)-1-ethanone oxime, and the mixture stirred until homogeneous (~5 minutes). p-Toluenesulfonyl chloride (2.04 g., 10.7 mmole) was added and the mixture stirred at room temperature under nitrogen for 1 hour. the mixture was added to a solution of potassium ethoxide (prepared by dissolving 430 mg. of potassium in 20 ml. of absolute ethanol) and the resulting mixture allowed to stir at room temperature for 0.5 hour. The resulting gelatinous suspension was diluted with 100 ml. of diethyl ether and stirred at room temperature for 30 minutes. The reaction was filtered through celite and the filtrate was concentrated. The residue was dissolved in 100 ml. of ether and any remaining solids filtered. The ether solution was extracted with 2 N hydrochloric acid (4×15 ml.) and the combined acid extracts concentrated to give a yellow solid. The residue was dissolved in 30 ml. of water containing 1.94 g. (20 mmoles) of potassium thiocyanate and the solution heated on a steam bath for 2 hours. After cooling, the mixture was made basic with sodium sodium carbonate and the precipitate filtered, washed with water and dried, 1.27 g. (58%), m.p. >260° C.

The NMR spectrum (DMSO-$D_6$) showed absorption at 7.82 (d, 1H), 7.48 (s, 1H), 6.9–6.2 (m, 4H), 3.18 (m, 2H) and 1.06 (t, 3H) ppm.

D. 2-ethylamino-4-(4-imidazolyl)pyridine

A mixture of 1.1 g. (5 mmoles) of 4-(2-ethylamino-4-pyridyl)imidazole-2-thiol and 4.0 g. of Raney nickel in 30 ml. of dimethylformamide was heated at 120° C. for 4 hours. The catalysts was filtered through celite and the filtrate concentrated under reduced pressure to remove the solvent. The residual oil solidified on trituration with diethyl ether affording 830 mg. (88%) of the desired product. Purification by chromatographing over 35 g. of silica gel using chloroform-methanol (19:1, v:v) as the eluent gave 384 g. (41%) of pure product, m.p. 135°–137° C.

Anal. Calc'd. for $C_{10}H_{12}N_4$: C, 63.8; H, 6.4; N, 29.8. Found: C, 63.4; H, 6.4; N, 29.4.

EXAMPLE III

Starting with 1-(2-chloro-4-pyridyl)-1-ethylenedioxyethane and the appropriate amine, and following the procedures of Examples IIA–D, the following compounds are prepared:

2-methylamino-4-(4-imidazolyl)pyridine;
2-n-propylamino-4-(4-imidazolyl)pyridine;
2-i-propylamino-4-(4-imidazolyl)pyridine;
2-benzylamino-4-(4-imidazolyl)pyridine; and
2-phenylpropylamino-4-(4-imidazolyl)pyridine.

EXAMPLE IV

2-Dimethylamino-4-(4-imidazolyl)pyridine

A. 2-dimethylaminoisonicotinonitrile

A mixture of 10 g. (72 mmoles) of 2-chloroisonicotinonitrile, 30 ml. of tetrahydrofuran, 100 ml. of toluene and 20 ml. (0.3 mole) of dimethylamine was placed in a steel bomb and heated at 190° C. for 4 hours. The bomb was cooled and the mixture removed and filtered. The residue, remaining after the filtrate was concentrated, was dissolved in water, which was subsequently extracted with ether (3×40 ml.). The combined extracts were dried and concentrated to the crude product. Recrystallization from petroleum ether gave 7.4 g. (69%) of the pure product, m.p. 63°–66° C.

B. 1-(2-dimethylamino-4-pyridyl)-1-ethanone

To a stirred solution of 7.4 g. (50 mmoles) of 2-dimethylaminoisonicotinonitrile in 150 ml. of diethyl ether was added dropwise 33 ml. (100 mmoles) of a 3 M solution of methyl magnesium bromide under a nitrogen atmosphere. On completion, the reaction was allowed to stir at room temperature for 16 hours, and was then quenched by the careful addition of 80 ml. of 2 N hydrochloric acid. The aqueous phase was separated and the organic phase extracted further with 2 N hydrochloric acid (2×10 ml.). The combined acid extracts were neutralized with solid sodium carbonate and extracted with chloroform (5×50 ml.). The combined chloroform extracts were dried and concentrated to a brown oil. Distillation of the residue gave 5.0 g. (61%) of the product as an oil (b.p. 110° C./1 torr). On standing the oil crystallized, m.p. 37°–42° C.

The NMR spectrum ($CDCl_3$) showed absorption at 8.24 (d, 1H), 6.86 (m, 2H), 3.08 (s, 6H) and 2.52 (s, 3H) ppm.

C. 1-(2-dimethylamino-4-pyridyl)-1-ethanone oxime

To 3.1 g. (45 mmoles) of hydroxylamine hyrochloride in 25 ml. of water and 22.5 ml. of 2 N sodium hydroxide solution was added 4.31 g. (26 mmoles) of 1-(2-dimethylamino-4-pyridyl)-1-ethanone, and the mixture was heated to boiling. After 5 minutes, methanol was added until the mixture became homogeneous. Heating was continued until a precipitate started to appear, and the mixture was then cooled. The solids were filtered, washed with water and dried. Recrystallization from toluene gave 4.03 g. (86%) of product, m.p. 145°–148° C.

Anal. Calc'd. for $C_9H_{13}N_3O$: C, 60.3; H, 7.3; N, 23.5. Found: C, 60.3; H, 7.4; N, 23.6.

D. 1-(dimethylamino-4-pyridyl)-1-ethanone oxime p-tosylate

A mixture of 4.0 g. (22 mmoles) of 1-(2-dimethylamino-4-pyridyl)-1-ethanone oxime and 4.8 g. (25 mmoles) of p-toluenesulfonyl chloride in 25 ml. of pyridine was stirred at room temperature for 24 hours. The mixture was poured into 250 ml. of water and the resulting precipitate was filtered, washed with water and dried in vacuo. Recrystallization from toluenecyclohexane gave 3.8 g. (52%) of the desired compound, m.p. 136° C. (dec.).

Anal. Calc'd. for $C_{16}H_{19}N_3O_3S$: C, 57.6; H, 5.7; N, 12.6. Found: C, 58.6; H, 5.8; N, 12.1.

E. 4-(2-dimethylamino-4-pyridyl)imidazle-2-thiol

To a solution of 10 ml. of ethanol in which was dissolved 400 mg. of potassium was added, under a nitrogen atmosphere, a mixture of 3.0 g. (9 mmoles) of 1-(2-dimethylamino-4-pyridyl)-1-ethanone oxime p-tosylate in 35 ml. of ethanol, and the resulting reaction mixture allowed to stir at room temperature for 1 hour. The mixture was diluted with 250 ml. of ether, the solids filtered and the filtrate concentrated. The residue was taken up in ether and extracted (3×20 ml.) with 2 N hydrochloric acid. The combined extracts were concentrated to a yellow solid. The residue was dissolved in 10 ml. of water and combined with a solution of 1.75 g. (18 mmoles) of potassium thiocyanate. The aqueous solution was heated on a steam bath for 2 hours, and the resulting precipitate was filtered from the cooled reaction. The solids were added to 40 ml. of a saturated sodium bicarbonate solution and stirred at room temperature for 15 minutes. The solid was filtered, washed with water and dried in vacuo, 1.4 g. (71%), m.p. >270° C.

The NMR spectrum showed absorption (DMSO-$D_6$) at 8.0 (s+d, 2H), 7.25 (s, 1H), 7.10 (d, 1H) and 3.2 (s, 6H).

F. 2-dimethylamino-4-(4-imidazolyl)pyridine

A mixture 800 mg. (3.63 mmoles) of 4-(2-dimethylamino-4-pyridyl)imidazole-2-thiol, 2 g. of Raney nickel and 20 ml. of dimethylformamide was heated at 120° C. for 3.5 hours. The catalyst was filtered and the filtrate concentrated to an oil which solidified on treatment with ether. The product was purified by chromatographing on 10 g. of florisil using chloroformmethanol (9:1, v:v) as the eluent, 361 mg., m.p. 173°–173.5° C.

Anal. Calc'd. for $C_{10}H_{12}N_4$: C, 63.8; H, 6.4; N, 29.8. Found: C, 63.6; H, 6.5; N, 29.6.

EXAMPLE V

Employing the procedures of Example IVA-F and starting with the appropriate amine and 2-chloroisonicotinonitrile, the following compounds are prepared:

2-methylethylamino-4-(4-imidazolyl)pyridine;
2-diethylamino-4-(4-imidazolyl)pyridine;
2-ethyl-n-propylamino-4-(4-imidazolyl)pyridine;
2-di-n-propylamino-4-(4-imidazolyl)pyridine;
2-ethyl-i-propylamino-4-(4-imidazolyl)pyridine;
2-di-i-propylamino-4-(4-imidazolyl)pyridine;
2-dibenzylamino-4-(4-imidazolyl)pyridine;
2-benzylmethylamino-4-(4-imidazolyl)pyridine.

EXAMPLE VI

2-Ethylamino-4-(2-amino-4-imidazolyl)pyridine

Sodium (370 mg., 15.5 mmoles) was dissolved in 25 ml. of absolute ethanol at room temperature under a nitrogen atmosphere and to this was added 2.7 g. (15 mmoles) of 1-(2-ethylamino-4-pyridyl)-1-ethanone oxime (Example IIB). The reaction mixture was stirred until homogeneous (5 minutes), then 3.0 g. (16 mmoles) of p-toluenesulfonyl chloride was added, and the mixture was stirred at room temperature under nitrogen for one hour. The mixture was subsequently added to a solution of potassium ethoxide (prepared by dissolving 630 mg. of potassium in 25 ml. of absolute ethanol) and the resulting mixture was stirred at room temperature under nitrogen for one hour. The resulting gelatinous suspension was diluted with 200 ml. of diethyl ether and filtered. The ether filtrate was extracted with (4×25 ml.) 2 N hydrochloric acid and the combined acid extracts concentrated to dryness. The residue was dissolved in 20 ml. of water, 1.35 g. (32 mmoles) of cyanamide was added and the mixture brought to pH 4.5 by the dropwise addition of 2 N sodium hydroxide solution. The mixture was heated at steam bath temperature for 1 hour, and was then cooled and made basic with concentrated ammonium hydroxide. The reaction mixture was concentrated to dryness and extracted with i-propanol. Removal of the i-propanol gave an oil which was taken up in 25 ml. of acetonitrile. Addition of diethyl ether to the acetonitrile solution resulted in the formation of a precipitate. Filtration and recrystallization of the solids from i-propanol gave 1.55 g. (52%) of the desired product, m.p. 200°–202° C.

The NMR spectrum showed absorption (DMSO-$D_6$) at 7.88 (d, 1H), 7.52 (d, 1H), 7.18 (b, 3H), 6.84 (s+d, 2H), 3.32 (m, 2H) and 1.17 (t, 3H) ppm.

EXAMPLE VII

Employing the procedure of Example VI, and starting with the appropriate 1-(2-alkyl- or phenylalkylamino-4-pyridyl)-1-ethanone oxime, the following compounds are prepared:
2-methylamino-4-(2-amino-4-imidazolyl)pyridine;
2-n-propylamino-4-(2-amino-4-imidazolyl)pyridine;
2-i-propylamino-4-(2-amino-4-imidazolyl)pyridine;
2-phenethylamino-4-(2-amino-4-imidazolyl)pyridine;
2-benzylamino-4-(2-amino-4-imidazolyl)pyridine; and
2-phenylpropylamino-4-(2-amino-4-imidazolyl)pyridine.

EXAMPLE VIII

2-Dimethylamino-4-(2-amino-4-imidazolyl)pyridine

Potassium (500 mg., 12.5 mmoles) was dissolved in 10 ml. of absolute ethanol at room temperature under a nitrogen atmosphere, and to the resulting solution was added a slurry of 3.8 g. (11 mmoles) of 1-(dimethylamino-4-pyridyl)-1-ethanone oxime p-tosylate (Example IVD) in 10 ml. of ethanol. The mixture was allowed to stir at room temperature for one hour during which time a thick precipitate formed. The mixture was diluted with 400 ml. of diethyl ether, filtered and the filtrate concentrated. The residue was dissolved in 100 ml. of ether and extracted (4×25 ml.) with 2 N hydrochloric acid. The combined acid extracts were concentrated to dryness and the residue dissolved in 30 ml. of water containing 1.35 g. (32 mmoles) of cyanamide. The pH was brought to 4.5 by the addition of 2 N sodium hydroxide solution and solution heated at steam bath temperature for 1 hour. The cooled reaction mixture was made basic with concentrated ammonium hydroxide and the resulting precipitate filtered, washed with water and dried in vacuo, 1.34 g. (58%), m.p. >270° C. The product was recrystallized from methanol.

Anal. Calc'd. for $C_{10}H_{13}N_5$: C, 59.1; H, 6.5; N, 34.5. Found: C, 58.6; H, 6.5; N, 33.9.

EXAMPLE IX

Starting with the requisite 1-(disubstituted amino-4-pyridyl)-1-ethanone oxime p-tosylate, and employing the procedure of Example VIII, the following compounds are prepared:
2-methylethylamino-4-(2-amino-4-imidazolyl)pyridine;
2-diethylamino-4-(2-amino-4-imidazolyl)pyridine;
2-ethyl-n-propylamino-4-(2-amino-4-imidazolyl)pyridine;
2-di-n-propylamino-4-(2-amino-4-imidazolyl)pyridine;
2-ethyl-i-propylamino-4-(2-amino-4-imidazolyl)pyridine;
2-di-i-propylamino-4-(2-amino-4-imidazolyl)pyridine;
2-dibenzylamino-4-(2-amino-4-imidazolyl)pyridine; and
2-benzylmethylamino-4-(2-amino-4-imidazolyl)pyridine.

EXAMPLE X

2-Ethylamino-4-(2-methyl-4-imidazolyl)pyridine

A. 2-(2-ethylamino-4-pyridyl)-2,2-diethoxyethylamine

To a solution of sodium ethoxide, formed by dissolving 740 mg. (32 mmoles) of sodium in 30 ml. of ethanol at room temperature under a nitrogen atmosphere, was added 5.38 g. (30 mmoles) of 1-(2-ethylamino-4-pyridyl)-1-ethanone oxime (Example IIB) and the resulting mixture stirred until homogeneous. p-Toluenesulfonyl chloride (6.1 g., 33 mmoles) was added and the mixture stirred for 1 hour at room temperature. The mixture was added directly to a solution of potassium ethoxide, prepared by dissolving 1.35 g. (35 mmoles) of potassium in 30 ml. of ethanol, and the mixture allowed to stir for 30 minutes at room temperature under a nitrogen atmosphere. The resulting gelatinous mass was diluted with 300 ml. of ether and the solids filtered. Hydrogen chloride gas was bubbled into the filtrate for 15 minutes and the mixture was then concentrated. The residue was dissolved in 250 ml. of water and made basic by the addition of solid sodium carbonate. The product was extracted with chloroform (3×40 ml.) and the combined extracts were dried over sodium sulfate and concentrated to give 7.6 g. (100%) of the desired intermediate as an oil.

The NMR spectrum showed absorption (CDCl$_3$) at 8.08 (d, 1H), 6.66 (s+d, 2H), 5.0 (b, 1H), 3.42 (q, 6H), 2.98 (s, 2H) and 1.19 (t, 9H) ppm.

B. 2-ethylamino-4-(2-methyl-4-imidazolyl)pyridine

A mixture of 2.0 g. (8 mmoles) of 2-(2-ethylamino-4-pyridyl)-2,2-diethoxyethylamine, 1.0 g. (8.3 mmoles) of ethyl acetimidate hydrochloride and 30 ml. of absolute ethanol was heated at reflux for 1.3 hours. The mixture was concentrated, and the residue taken up in 10 ml. of concentrated hydrochloric acid. The acid solution was heated on a steam bath for one hour and the cooled reaction made basic by the addition of solid potassium carbonate. The product was extracted with chloroform (4×15 ml.) and the combined extracts dried and concentrated to give 1.1 g. of crude product. The product was chromatographed over 35 g. of silica gel using chloroform-methanol (19:1, v:v) as the eluent to give 510 mg. (30%), m.p. 214°–216° C.

Anal. Calc'd. for $C_{11}H_{14}N_4$: C, 65.3; H, 7.0; N, 27.7. Found: C, 64.8; H, 7.1; N, 26.7.

EXAMPLE XI

2-Ethylamino-4-(2-ethyl-4-imidazolyl)pyridine

The procedure of Example XB was employed, starting with 2.0 g. (8 mmoles) of 2-(2-ethylamino-4-pyridyl)-2,2-diethoxyethylamine and 1.16 g. (8.3 mmoles) of ethyl propionimidate hydrochloride in 30 ml. of ethanol, to give 605 g. (33%) of the title compound as a white solid, 190°–193° C.

The NMR spectrum showed absorption (CDCl$_3$) at 8.01 (d, 1H), 7.33 (s, 1H), 6.86 (s+d, 2H), 3.23 (q, 2H), 2.82 (q, 2H), and 1.22 (t, 6H), ppm.

Anal. Calc'd for $C_{12}H_{16}N_4 \cdot 1/4 H_2O$: C, 65.3; H, 7.5; N, 25.4. Found: C, 65.5; H, 7.4; N, 25.6.

EXAMPLE XII

Starting with the appropriate 1-(2-alkylamino-4-pyridyl)-1-ethanone oxime and requisite ethyl alkylimidate, and employing the procedures of Example XA-B, the following compounds are prepared:

| $R_1$ | $R_2$ | $R_3$ |
|---|---|---|
| CH$_3$— | H— | CH$_3$— |
| C$_2$H$_5$— | H— | CH$_3$— |
| CH$_3$— | H— | n-C$_3$H$_7$— |
| C$_2$H$_5$— | H— | n-C$_3$H$_7$— |
| CH$_3$— | H— | i-C$_3$H$_7$— |
| n-C$_3$H$_7$— | H— | CH$_3$— |
| i-C$_3$H$_7$— | H— | C$_2$H$_5$— |
| n-C$_3$H$_7$— | H— | n-C$_3$H$_7$— |
| CH$_3$— | H— | C$_6$H$_5$CH$_2$— |
| CH$_3$— | H— | C$_6$H$_5$CH(CH$_3$)— |
| C$_2$H$_5$— | H— | C$_6$H$_5$(CH$_2$)$_3$— |
| n-C$_3$H$_7$— | H— | C$_6$H$_5$CH$_2$— |

EXAMPLE XIII

2-Dimethylamino-4-(2-methyl-4-imidazolyl)pyridine

A. 2-(2-dimethylamino-4-pyridyl)-2,2-diethoxyethylamine

To a solution of sodium ethoxide, formed by dissolving 740 mg. (32 mmoles) of sodium metal in 35 ml. of ethanol at room temperature under a nitrogen atmosphere, is added 5.38 g. (30 mmoles) of 1-(2-dimethylamino-4-pyridyl)-1-ethanone oxime (Example IVC) and the resulting mixture subsequently stirred until homogeneous. p-Toluenesulfonyl chloride (6.1 g., 33 mmoles) is added and the mixture allowed to stir at room temperature for 1 hour. The mixture is added to a solution of potassium ethoxide (1.35 g. potassium in 30 ml. ethanol) and the mixture then allowed to stir for 1 hour at room temperature. Ether (300 ml.) is added to the resulting gelatinous mass and the solids filtered. Hydrogen chloride gas is bubbled into the filtrate for 15 minutes, and the mixture is concentrated. The residue is dissolved in 250 ml. of water, which is then made basic with solid sodium carbonate. The product is extracted with chloroform (3×50 ml.), and the combined extracts are dried over sodium sulfate and concentrated to give the product.

B. 2-dimethylamino-4-(2-methyl-4-imidazolyl)pyridine

A mixture of 1.0 g. (4 mmoles) of 2-(2-dimethylamino-4-pyridyl)-2,2-diethoxyethylamine, 500 mg. (4.1 mmoles) of ethyl acetimidate hydrochloride and 15 ml. of ethanol is heated to reflux for 1.5 hours. The mixture is concentrated, and the residue taken up in 10 ml. of concentrated hydrochloric acid. After heating at steam bath temperatures for 1 hour, the cooled acid solution is made basic by the addition of solid sodium carbonate, and the product is extracted with chloroform (3×10 ml.). The combined extracts are dried and concentrated to give the crude product, which is purified further by chromatographing on silica-gel using chloroform-methanol as the eluent.

EXAMPLE XIV

Starting with the requisite 1-(2-disubstituted-4-pyridyl)-1-ethanone oxime and ethyl alkylimidate and using the procedures of Examples XIIIA–B the following compounds are prepared:

| $R_1$ | $R_2$ | $R_3$ |
|---|---|---|
| $CH_3-$ | $CH_3-$ | $C_2H_5-$ |
| $i\text{-}C_3H_7-$ | $CH_3-$ | $C_2H_5-$ |
| $CH_3-$ | $C_2H_5-$ | $C_2H_5-$ |
| $C_2H_5-$ | $C_2H_5-$ | $C_2H_5-$ |
| $CH_3-$ | $C_2H_5-$ | $n\text{-}C_3H_7$ |
| $n\text{-}C_3H_7-$ | $C_2H_5-$ | $n\text{-}C_3H_7-$ |
| $n\text{-}C_3H_7-$ | $n\text{-}C_3H_7-$ | $n\text{-}C_3H_7-$ |
| $CH_3-$ | $C_2H_5-$ | $i\text{-}C_3H_7-$ |
| $C_2H_5-$ | $C_2H_5-$ | $i\text{-}C_3H_7$ |
| $CH_3-$ | $i\text{-}C_3H_7$ | $i\text{-}C_3H_7$ |
| $CH_3-$ | $C_6H_5CH_2-$ | $C_6H_5CH_2-$ |
| $C_2H_5-$ | $C_6H_5CH_2-$ | $C_6H_5CH_2-$ |
| $CH_3$ | $CH_3-$ | $C_6H_5CH_2-$ |
| $i\text{-}C_3H_7-$ | $CH_3-$ | $C_6H_5CH_2-$ |

EXAMPLE XV

2-Amino-4-(2-methyl-4-imidazolyl)pyridine

A. 2-(2-amino-4-pyridyl)-2,2-diethoxyethylamine

To a solution of sodium ethoxide, prepared by dissolving 740 mg. (32 mmoles) of sodium in 35 ml. of ethanol at room temperature under a nitrogen atmosphere, is added 4.53 g. (30 mmoles) of 1-(2-amino-4-pyridyl)-1-ethanone oxime (Example IIE). To the resulting solution is then added 6.1 g. (33 mmoles) of p-toluenesulfonyl chloride and the mixture allowed to stir at room temperature for 1 hour. The resulting mixture is then added to a solution of potassium ethoxide (1.35 g. of potassium in 30 ml. ethanol) and the reaction mixture allowed to stir an additional hour at room temperature. The resulting gelatinous precipitate is treated with 300 ml. of diethyl ether and the solids are filtered. After gaseous hydrogen chloride has been bubbled into the reaction mixture for 15 minutes, the mixture is concentrated and the residue dissolved in 250 ml. of water. The aqueous solution is made basic with solid sodium carbonate and the liberated product extracted with chloroform (3×15 ml.). The combined extracts are dried and concentrated to give the product.

B. 2-amino-4-(2-methyl-4-imidazolyl)pyridine

A mixture of 890 mg. (4 mmoles) of 2-(2-amino-4-pyridyl)-2,2-diethoxyethylamine, 500 mg. (4.1 mmoles) of ethyl methylimidate hydrochloride and 15 ml. of ethanol is heated to reflux for 1.5 hours. The mixture is concentrated and the residue taken up in 10 ml. of concentrated hydrochloric acid. After heating on a steam bath for 1 hour, the cooled acid solution is made basic with solid sodium carbonate, and the product is extracted with chloroform (3×10 ml.). The combined, dried extracts are concentrated to dryness and the residue purified by chromatographing on silica gel using chloroform-methanol as the eluent.

EXAMPLE XVI

2-Methyl-4-(2-methyl-4-imidazolyl)pyridine

A. 2-methyl-4-acetylpyridine

A solution of 3.5 g. (29.7 mmoles) of 2-methyl-4-cyanopyridine in 20 ml. of dry ether was added dropwise to a cooled (5° C.) solution of 20 ml. of 3.0 M methyl magnesium bromide in ether. After addition was complete the mixture was allowed to warm to room temperature and stirred for 18 hours. The reaction mixture was cooled to 5° C. and the excess Grignard reagent decomposed by the addition of water. The mixture was acidified with 6 N hydrochloric acid and the aqueous phase was separated. The ether phase was again extracted with 30 ml. of 1 N hydrochloric acid and the combined aqueous extracts were warmed on a steam bath for one hour. The aqueous solution was cooled, made basic with solid sodium bicarbonate and extracted with (3×100 ml.) ether. The combined ether extracts were dried and evaporated to give 2.1 g. (53%) of a yellow oil. b.p. 50°–53° C. (0.3 torr).

The NMR spectrum (CDCl$_3$) showed absorption at 8.58 (d, 1H), 7.46 (s, 1H), 7.38 (d, 1H), 2.53 (s, 3H) and 2.48 (s, 3H) ppm.

B. 2-methyl-4-acetylpyridine oxime

To 4.03 g. (58.4 mmoles) of hydroxylamine hydrochloride in 27 ml. of a 2 N sodium hydroxide solution was added 3.95 g. (29.2 mmoles) of 2-methyl-4-acetylpyridine and the resulting mixture heated on a steam bath, methanol being added to keep the mixture homogeneous. The mixture was heated for an additional 5 minutes and was then cooled. The resulting precipitate was filtered, washed with water and dried 3.95 g. (90%), m.p. 151°–152° C.

The NMR spectrum (DMSO-D$_6$) showed absorption at 11.42 (s, 1H), 8.38 (d, 1H), 7.37 (s, 1H), 7.30 (s, 1H), 2.52 (s, 3H), and 2.17 (s, 3H), ppm.

C. 2-methyl-4-acetylpyridine oxime tosylate

To a mixture of 3.95 g. (26.3 mmoles) of 2-methyl-4-acetylpyridine oxime in 25 ml. of dry pyridine was added 5.87 (30.9 mmoles) of toluenesulfonyl chloride and the reaction mixture stirred at room temperature for 48 hours. The reaction mixture was diluted with 35 ml. of water and the resulting precipitate was filtered, washed with water and dried in vacuo, 8.0 g. (81%), m.p. 95°–96° C.

The NMR spectrum (CDCl$_3$) showed absorption at 8.42 (d, 1H), 7.82 (d, 2H), 7.4–7.1 (m, 4H), 2.50 (s, 3H), 2.42 (s, 3H), and 2.30 (s, 3H) ppm.

D. 2-methyl-4-(2-methyl-4-imidazolyl)pyridine

To 570 mg. (14.2 mmoles) of potassium metal dissolved in 10 ml. of absolute ethanol was added a mixture of 4.33 g. (14.2 mmoles) of 2-methyl-4-acetylpyridine oxime tosylate in 20 ml. of absolute ethanol and the resulting mixture stirred at room temperature for 1.5 hours. The reaction was quenched with 100 ml. of ether and the potassium tosylate removed by filtration. Gaseous hydrogen chloride was bubbled into the filtrate for 5 minutes and the solution was concentrated. The residue was dissolved in 50 ml. of water and the solution was made basic with solid potassium carbonate. The aqueous was extracted with (5×20 ml.) chloroform and the combined organic extracts dried and concentrated to dryness giving an oil. The residual oil was dissolved in 25 ml. of methanol, 1.75 g. (14.2 mmoles) of ethyl acetimidate hydrochloride was added and the mixture was heated to reflux for 1.5 hours. The mixture was concentrated and the residue taken up in 25 ml. of concentrated hydrochloric acid. The acid solution was heated on a steam bath for one hour, then allowed to stir at room temperature for 18 hours. The mixture was made basic with solid potassium carbonate and was extracted with (2×50 ml.) chloroform and (1×50 ml.) ethyl acetate. The combined extracts were dried and evaporated leaving an oil which solidified on trituration with a toluene/cyclohexane/acetone mixture, 530 mg. (22%), m.p. 115°–117° C.

Anal. Calc'd. for C$_{10}$H$_{11}$N$_3$: C, 69.3; H, 6.4; N, 24.3. Found: C, 68.5; H, 6.4; N, 23.9.

EXAMPLE XVII

2-Methyl-4-(2-amino-4-imidazolyl)pyridine

To 210 mg. of potassium metal dissolved in 10 ml. of absolute ethanol was added a suspension of 1.46 (4.8 mmoles) of 2-methyl-4-acetylpyridine oxime tosylate in 10 ml. of dry ethanol, and the mixture allowed to stir at room temperature for one hour. Ether (200 ml.) was added, the potassium tosylate filtered, and the filtrate extracted with (3×20 ml.) 1 N hydrochloric acid. The combined acid extracts were concentrated to a yellow solid, which was then dissolved in 30 ml. of water. Cyanamide (600 mg., 14.2 mmoles) was dissolved in the aqueous solution and the pH adjusted to 4.5 by the addition of 2 N sodium hydroxide. The solution was heated on a steam bath for one hour, cooled in an ice bath and made basic with concentrated ammonium hydroxide. The mixture was concentrated, and the residue triturated with 15 ml. of ethanol. The solids were filtered and the filtrate was treated with ether. The resulting precipitate was filtered and dried in vacuo, 755 mg. (90%), m.p. 226°–228° C.

The NMR spectrum (DMSO-D$_6$) showed absorption at 8.40 (d, 1H), 7.50 (dts, 2H), 6.0 (broad) and 2.54 (s, 3H) ppm.

EXAMPLE XVIII

The non-toxic hydrohalide acid addition salts of each of the previously reported 2-ethylamino-4-(2-amino-4-imidazolyl)pyridine base compounds of this invention, such as the corresponding hydrochloride, hydrobromide and hydroiodide salts, are each individually prepared by first dissolving the respective organic base compound in absolute ether followed by the introduction of the appropriate hydrohalide gas into the reaction solution until saturation of same is complete with respect to said gas, whereupon the desired acid addition salt soon precipitates from said solution. In this way, 1.0 g. of 2-ethylamino-4-(2-amino-4-imidazolyl)pyridine, obtained as a free base product in Example VI, is converted via dry hydrogen chloride gas to the corresponding dihydrochloric acid addition salt in substantially quantitative yield.

EXAMPLE XIX

The nitrate, sulfate or bisulfate, phosphate or acid phosphate, acetate, lactate, maleate, fumerate, citrate or acid citrate, tartrate or bitartrate, succinate, gluconate, saccharate, methanesulfonate, ethanesulfonate, benzenesulfonate and p-toluenesulfonate salts of each of the aforementioned 2-ethylamino-4-(2-amino-4-imidazolyl)pyridine base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition salt therefrom. In this manner, equimolar amounts of 2-ethylamino-4-(2-methyl-4-imidazolyl)pyridine and concentrated sulfuric acid react to afford the corresponding sulfuric acid addition salt. In like manner, each of the other salts is similarly prepared.

EXAMPLE XX

A dry pharmaceutical composition is prepared by blending the following materials together in the proportions by weight specified below:

| | |
|---|---|
| 2-ethylamino-4-(2-methyl-4-imidazolyl)pyridine | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 200 mg. of the active ingredient. Other tablets are also prepared in a similar fashion containing 25, 50 and 100 mg. of the active ingredient, respectively, merely using the appropriate amount of the 2-ethylamino-4-(2-methyl-4-imidazolyl)pyridine salt in each case.

EXAMPLE XXI

A dry solid pharmaceutical composition is prepared by combining the following materials together in the proportions by weight indicated:

| | |
|---|---|
| 2-ethylamino-4-(2-amino-4-imidazolyl)pyridine | 50 |

| -continued | |
|---|---|
| Polyethylene glycol, average molecular weight 4000 | 30 |

The dried mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

We claim:

1. A compound selected from the group consisting of pyridylimidazoles of the formulae:

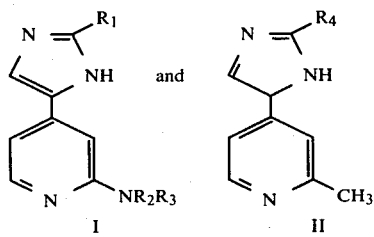

and the pharmaceutically acceptable acid addition salts thereof, wherein $R_1$ is selected from the group consisting of hydrogen, alkyl having one to three carbon atoms and amino; $R_2$ and $R_3$ are each selected from the group consisting of hydrogen, alkyl having one to three carbon atoms and phenylalkyl wherein said alkyl contains from one to three carbon atoms; and $R_4$ is selected from the group consisting of methyl and amino.

2. A compound of claim 1, formula I, wherein $R_2$ is hydrogen and $R_3$ is alkyl having from one to three carbon atoms.

3. The compound of claim 2 wherein $R_1$ is amino and $R_3$ is ethyl.

4. The compound of claim 2 wherein $R_1$ is hydrogen and $R_3$ is ethyl.

5. The compound of claim 2 wherein $R_1$ is methyl and $R_3$ is ethyl.

6. The compound of claim 2 wherein $R_1$ and $R_3$ are each ethyl.

7. A compound of claim 1, formula I, wherein $R_2$ and $R_3$ are each alkyl having from one to three carbon atoms.

8. The compound of claim 7 wherein $R_1$ is hydrogen and $R_2$ and $R_3$ are each methyl.

9. The compound of claim 7 wherein $R_1$ is amino and $R_2$ and $R_3$ are each methyl.

10. A compound of claim 1, formula I, wherein $R_2$ and $R_3$ are each hydrogen.

11. The compound of claim 10 wherein $R_1$ is hydrogen.

12. The compound of claim 1, formula II, wherein $R_4$ is methyl.

13. The compound of claim 1, formula II, wherein $R_4$ is amino.

14. A pharmaceutical composition suitable for oral administration comprising a pharmaceutically acceptable carrier and a therapeutically-effective amount of an anti-ulcer agent wherein said agent is a compound as claimed in claim 1.

* * * * *